US010590491B2

(12) United States Patent
Hamilton et al.

(10) Patent No.: US 10,590,491 B2
(45) Date of Patent: *Mar. 17, 2020

(54) MOLECULAR MARKERS ASSOCIATED WITH MAL DE RIO CUARTO VIRUS IN MAIZE

(71) Applicant: Agrigenetics, Inc., Indianapolis, IN (US)

(72) Inventors: Jennifer L. Hamilton, Indianapolis, IN (US); Juan P. Raimondi, Buenos Aires (AR); Trisha Borowicz, Greenfield, IN (US); Cherie Ochsenfeld, Brownsburg, IN (US); James W. Bing, Zionsville, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/647,044

(22) Filed: Jul. 11, 2017

(65) Prior Publication Data
US 2017/0314084 A1    Nov. 2, 2017

Related U.S. Application Data

(63) Continuation of application No. 14/585,012, filed on Dec. 29, 2014, now Pat. No. 9,702,015.

(60) Provisional application No. 61/920,859, filed on Dec. 26, 2013.

(51) Int. Cl.
*A01H 5/10*       (2018.01)
*C12Q 1/6895*  (2018.01)

(52) U.S. Cl.
CPC ............ *C12Q 1/6895* (2013.01); *A01H 5/10* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 9,702,015 B2 * | 7/2017 | Hamilton | C12Q 1/6895 |
| 2006/0141495 A1 | 6/2006 | Wu | |
| 2010/0223293 A1 | 9/2010 | Butruille et al. | |
| 2010/0325750 A1 * | 12/2010 | Martin | A01H 5/10 |
| | | | 800/265 |

OTHER PUBLICATIONS

*Zea mays* sequence PZA02272-75311-GT119, genomic sequence tagged site, NCBI/GenBank accession No. BV152977, published May 11, 2004.*
Civardi et al., 1994, Proc. Natl. Acad. Sci. USA 91: 8268-8272.*

* cited by examiner

*Primary Examiner* — Bratislav Stankovic
(74) *Attorney, Agent, or Firm* — Magleby Cataxinos & Greenwood

(57) ABSTRACT

This invention relates to methods for identifying maize plants that having increased MRCV resistance. The methods use molecular markers to identify and to select plants with increased MRCV resistance. Maize plants generated by the methods of the invention are also a feature of the invention.

9 Claims, No Drawings
Specification includes a Sequence Listing.

SEQUENCE LISTING

<160> NUMBER OF SEQ ID NOS: 9

<210> SEQ ID NO 1
<211> LENGTH: 121
<212> TYPE: DNA
<213> ORGANISM: Zea mays

<400> SEQUENCE: 1

```
gggttttgaa ggcgaagtgg acggaaccac agcctttaga ggttcagttg caggttttct    60
rtggagaatt ggtccagctg aaggtttgtt ctcgaggacc agtttggttg ctggttgktc   120
a                                                                   121
```

<210> SEQ ID NO 2
<211> LENGTH: 201
<212> TYPE: DNA
<213> ORGANISM: Zea mays

<400> SEQUENCE: 2

```
ataacccaga tgaataaccc aggctctatg tatgacttca cggctaggat aaaatcaggg    60
ttgttgggc ttagctataa gagcacccag attctcaacg wtgatcctat agagccgact   120
caagtataat tctcgagcct acaaaaagtc ttccaaccaa caacaaattt ccgcacacta   180
catactcaga aagtaaaaaa a                                             201
```

<210> SEQ ID NO 3
<211> LENGTH: 201
<212> TYPE: DNA
<213> ORGANISM: Zea mays

<400> SEQUENCE: 3

```
ggcagggaag agacaagcgc cggagccaga gaagcctgcg gccaggccac taggccaggg    60
tactccgggg aggcgaggga gcgcttgagg gcaacaggta sgagaagtga ggtgactgct   120
atgaatccta tttattttcc aaatattcat ttgttttgac acctttcatt ttttttcttt   180
ctgaaaggaa attgcattttt c                                            201
```

<210> SEQ ID NO 4
<211> LENGTH: 201
<212> TYPE: DNA
<213> ORGANISM: Zea mays

<400> SEQUENCE: 4

```
tctcttacag tttcagtttt cccaggtcaa tcttctgctt agggtatgtg taggcttcgt    60
agtttatctt ctggccaagg gagctcagct ttgtgagtgt rgttatcagg tcaacctgtc   120
atacataaca aacaagcaca agtcagaata gctgtgcact gccagcgcat acagatcaat   180
gagtccttac ctcatagtca g                                             201
```

<210> SEQ ID NO 5
<211> LENGTH: 201
<212> TYPE: DNA
<213> ORGANISM: Zea mays

```
<400> SEQUENCE: 5
gcaacaactg ttttgtcaag ctttatctgc tgcagtgata agactgctcc taaaccatgc      60
acgcccaaaa gcgcagcgtg aatgacagcg atcaatcccc rcttttgtca gtctaagcta     120
gcagctcatg catgccttgc ctgccggcct gctcacgaga cacggcgtcg agttcctcgc     180
tcttgtggcc tcatgcatat c                                               201

<210> SEQ ID NO 6
<211> LENGTH: 121
<212> TYPE: DNA
<213> ORGANISM: Zea mays

<400> SEQUENCE: 6
tggtcaaatt gtttgcctct gtggtcgtgc actcgtgcat gcatgcggac agtgcccatg      60
mttcagtcat gttgagttga gttctgcttg ccggcctgtg atgttatytg ttcttgttca     120
a                                                                     121

<210> SEQ ID NO 7
<211> LENGTH: 201
<212> TYPE: DNA
<213> ORGANISM: Zea mays

<400> SEQUENCE: 7
tataccttgc ttgctttgct tacctagagc tagctagcgc cggatcgcta agctgctagc      60
tttctttaaa gctaataata aagttgtcac gcggattaaa watagcgcaa ctgggagtac     120
gagtcactgt ccttggaacc accactggtc gcacgcagac gcagctgcta gctgtgccca     180
agatctagct agctagccag g                                               201

<210> SEQ ID NO 8
<211> LENGTH: 121
<212> TYPE: DNA
<213> ORGANISM: Zea mays

<400> SEQUENCE: 8
tcttgcgcag gcagagaggc aacagcgttt cgtatcgttc gttgctatgg ttcgtccaat      60
yaagttcgga aaacccatga acgtgtgatg atgaccagtg tcaaacaaga agcgtgctag     120
t                                                                     121

<210> SEQ ID NO 9
<211> LENGTH: 121
<212> TYPE: DNA
<213> ORGANISM: Zea mays

<400> SEQUENCE: 9
tcgactagtc gagtttcctt tttgtgttta gtatgatggt tgggcacgtg ctggtaccga      60
rcgtgcttca ctcattatag tattttgatt cttgaacaaa ttgtgtgttg ggctaaacca     120
t                                                                     121
```

MOLECULAR MARKERS ASSOCIATED WITH MAL DE RIO CUARTO VIRUS IN MAIZE

CROSS-REFERENCE TO RELATED APPLICATION

This application is a continuation of U.S. patent application Ser. No. 14/585,012 filed on Dec. 29, 2014, now issued U.S. Pat. No. 9,702,015, which claims the benefit of U.S. Provisional Patent Application Ser. No. 61/920,859, filed Dec. 26, 2013, the disclosures of which are hereby incorporated herein in their entirety by this reference.

FIELD OF THE INVENTION

The present invention relates to methods useful in selecting for increased Mal de Rio Cuarto Virus resistance in maize plants.

BACKGROUND OF THE INVENTION

Mal de Rio Cuarto Virus (MRCV) is considered to be the most prevalent and destructive viral disease of maize, *Zea mays* L., in Argentina. MRCV infection causes abnormal corn development and significantly reduces crop yield. The susceptible phenotype includes stunting, shortened internodes, cut and reduced leaves, deformed tassels with no anthers, reduced roots, underdeveloped ears with poor kernel sets and overall thickening of vascular tissues. The largest known outbreak of MRCV in Argentina to date occurred during the 1996/1997 growing season and affected nearly 300,000 hectares producing approximately $120MM in yield losses. MRCV disease is vectored by the leafhopper *Delphacodes kuscheli*. Increased populations of *D. kuscheli* in 2006 apparently led to a reoccurrence of the viral disease in Argentinean corn plants, which significantly affected the 2007 harvest. Exploratory methods to control the disease using pesticides and other means of insect control have been unsuccessful and development of MCRV tolerant lines through selective breeding is a primary initiative for seed producers.

As *Bacillus thuringiensis* (Bt) technology becomes more widespread in Brazil and Northern Argentina, the amount of insecticide used on corn crops will most likely decrease. This reduction in insecticide may increase the numbers of leaf hoppers in the environment, thus amplifying MRCV disease pressure. Breeding resistance into corn is the principal and most effective control method to manage yield loss associated with MRCV disease. The development of molecular genetic markers has facilitated mapping and selection of agriculturally important traits in maize, and quantitative trait loci (QTL) for MRCV resistance have been identified. QTL conferring resistance to MRCV have been identified on chromosomes 1 and 8 (DiRenzo et al. 2004; Kreff et al. 2006), chromosome 2 (WO 2009/058335), and chromosomes 4 and 10 (Kreff et al. 2006). Introgression of QTL through the use of molecular markers associated with MRCV will increase the speed and accuracy of moving MRCV resistance into elite corn hybrids, thus improving the level of resistance in subtropical germplasm. Incorporating MRCV resistance into elite corn germplasm may prevent the spread of the viral disease to non-endemic regions.

Despite the fact that information for MRCV resistance QTL is available in the art, few pedigrees can be classified as highly tolerant and there is little evidence of any strong resistance to MRCV in commercially available hybrids. There is a need for commercially acceptable hybrids that are MRCV resistant and for a method to develop and track resistant maize inbreds and hybrids through marker assisted breeding.

Described within is a method to map MRCV resistance QTL in a DH population using a bi-parental QTL mapping approach. The present invention allows selection of progeny which contain the genomic background of the agronomically desirable parent and the genomic trait of the MRCV resistant donor parent. The present invention also allows tracking of MRCV resistance QTL in order to introgress the MRCV resistance trait into new plants through traditional breeding.

SUMMARY OF THE INVENTION

One embodiment of the present invention is a method for selecting a plant having increased MRCV resistance. The method includes the steps of: a) detecting at least one marker nucleic acid; and, b) selecting a plant comprising the marker nucleic acid, thereby selecting a plant having increased MRCV resistance. The plant is preferably a maize plant.

In embodiments of the invention, the marker nucleic acid is selected from the group consisting of PZA02272-3, DAS-PZ-11980, DAS-PZ-8644, DAS-PZ-10816, DAS-PZ-2849, zfl2-9, DAS-PZ-19494, Mo17-11696, and MAGI_105144. In further embodiments of the invention, at least one marker nucleic acid is selected, and preferably, at least two marker nucleic acids are selected.

In another embodiment of the invention is a method for selecting a maize plant having increased MRCV resistance, the method comprising: a) detecting at least one marker nucleic acids, wherein at least one marker nucleic acid is selected from the group consisting of PZA02272-3, DAS-PZ-11980, DAS-PZ-8644, DAS-PZ-10816, DAS-PZ-2849, zfl2-9, DAS-PZ-19494, Mo17-11696, and MAGI_105144; and, b) selecting a plant comprising at least one marker nucleic acids, thereby selecting a maize plant having increased MRCV resistance. Maize plants obtained by the methods described herein are also contemplated by the present invention.

BRIEF DESCRIPTION OF FIGURES AND SEQUENCE LISTINGS

The invention can be more fully understood from the following detailed description and the accompanying drawings and Sequence Listing, which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

SEQ ID NO: 1 contains the PZA02272-3 SNP and flanking sequence.

SEQ ID NO: 2 contains the DAS-PZ-11980 SNP and flanking sequence.

SEQ ID NO: 3 contains the DAS-PZ-8644 SNP and flanking sequence.

SEQ ID NO: 4 contains the DAS-PZ-10816 SNP and flanking sequence.

SEQ ID NO: 5 contains the DAS-PZ-2849 SNP and flanking sequence.

SEQ ID NO: 6 contains the zfl2-9 SNP and flanking sequence.

SEQ ID NO: 7 contains the DAS-PZ-19494 SNP and flanking sequence.

SEQ ID NO: 8 contains the Mo17-11696 SNP and flanking sequence.

SEQ ID NO: 9 contains the MAGI_105144 SNP and flanking sequence.

DETAILED DESCRIPTION OF THE INVENTION

The present invention provides methods for identifying and selecting maize plants with increased MRCV resistance. The following definitions are provided as an aid to understand the invention.

The term "allele" refers to one of two or more different nucleotide sequences that occur at a specific locus.

An "amplicon" is amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid for a transcribed form thereof are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to bacterial artificial clones (BACs) and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is linked to it and when the presence of the allele is an indicator that the desired trait or trait form will occur in a plant comprising the allele.

The "B73 reference genome, version 2" is the physical and genetic framework of the maize B73 genome. It is the result of a sequencing effort utilizing a minimal tiling path of approximately 19,000 mapped BAC clones, and focusing on producing high-quality sequence coverage of all identifiable gene-containing regions of the maize genome. These regions were ordered, oriented, and along with all of the intergenic sequences, anchored to the extant physical and genetic maps of the maize genome. It can be accessed using a genome browser, the Maize Genome Browser, which is publicly available on the internet and facilitates user interaction with sequence and map data.

A "bacterial artificial chromosome (BAC)"is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation: the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

"Chromosomal interval" designates a contiguous linear span of genomic DNA that resides in plants on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%, respectively.

The term "chromosomal interval" designates any and all intervals defined by any of the markers set forth in this invention. A chromosomal interval that correlates with increased MRCV resistance is provided. This interval, located on chromosome 2, comprises and is flanked by PZA02272-3 and MAGI_105144. A subinterval of chromosomal interval PZA02272-3 and MAGI_105144 is DAS-PZ-2849 and DAS-PZ-19494.

The term "complement" refers to a nucleotide sequence that is complementary to a given nucleotide sequence, i.e., the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

The term "elite line" refers to any line that has resulted from breeding and selection for superior agronomic performance. An elite plant is any plant from an elite line.

A "favorable allele" is the allele at a particular locus that confers, or contributes to, a desirable phenotype, e.g., increased MRCV resistance, or alternatively, is an allele that allows the identification of plants with decreased MRCV resistance that can be removed from a breeding program or planting ("counter-selection"). A favorable allele of a marker is a marker allele that segregates with the favorable phenotype, or alternatively, segregates with the unfavorable plant phenotype, therefore providing the benefit of identifying plants.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of molecular genetic markers (also called molecular markers). A genetic map is a product of the mapping population, types of markers used, and the polymorphic potential of each marker between different populations. The order and genetic distances between loci can differ from one genetic map to another. However, information such as marker position and order can be correlated between maps by determining the physical location of the markers on the chromosome of interest, using the B73 reference genome, version 2, which is publicly available on the internet. One of ordinary skill in the art can use the publicly available genome browser to determine the physical location of markers on a chromosome.

The term "Genetic Marker" shall refer to any type of nucleic acid based marker, including but not limited to, Restriction Fragment Length Polymorphism (RFLP) (Botstein et al, 1998), Simple Sequence Repeat (SSR) (Jacob et al., 1991), Random Amplified Polymorphic DNA (RAPD) (Welsh et al., 1990), Cleaved Amplified Polymorphic Sequences (CAPS) (Rafalski and Tingey, 1993, Trends in Genetics 9:275-280), Amplified Fragment Length Polymorphism (AFLP) (Vos et al, 1995, Nucleic Acids Res. 23:4407-4414), Single Nucleotide Polymorphism (SNP) (Brookes, 1999, Gene 234:177-186), Sequence Characterized Amplified Region (SCAR) (Pecan and Michelmore, 1993, Theor. Appl. Genet, 85:985-993), Sequence Tagged Site (STS) (Onozaki et al. 2004, Euphytica 138:255-262), Single Stranded Conformation Polymorphism (SSCP) (Orita et al., 1989, Proc Natl Aced Sci USA 86:2766-2770). Inter-Simple Sequence Repeat (ISR) (Blair et al. 1999, Theor. Appl. Genet. 98:780-792), Inter-Retrotransposon Amplified Polymorphism (TRAP), Retrotransposon-Microsatellite Amplified Polymorphism (REMAP) (Kalendar et al., 1999, Theor. Appl. Genet 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple led, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence, polymorphisms at a particular locus, such as a single marker locus, or sequence polymorphisms at multiple loci along a chromosomal segment in a given genome. The former can also be referred to as "marker haplotypes" or "marker alleles", while the latter can be referred to as "long-range haplotypes".

The "heritability ($h^2$)" of a trait within a population is the proportion of observable differences in a trait between individuals within a population that is due to genetic differences. The $h^2$ value of the QTL is a percentage of variation that is explained by genetics, instead of environment.

A "heterotic group" comprises a set of genotypes that perform well when crossed with genotypes from a different heterotic group (Hallauer at al. (1998) Corn breeding, p. 463-564. In G. F. Sprague and J. W. Dudley (ed) Corn and corn improvement). Inbred lines are classified into heterotic groups, and are further subdivided into families within a heterotic group, based on several criteria such as pedigree, molecular marker-based associations, and performance in hybrid combinations (Smith at al. (1990) Theor. Appl. Gen. 80:833-840). The two most widely used heterotic groups in the United States are referred to as "Iowa Stiff Stalk Synthetic" (BSSS) and "Lancaster" or "Lancaster Sure Crop" (sometimes referred to as NSS, or Iron-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

"Hybridization" or "nucleic acid hybridization" refers to the pairing of complementary RNA and DNA strands as well as the pairing of complementary DNA single strands.

The term "hybridize" means the formation of base pairs between complementary regions of nucleic acid strands.

The term "indel" refers to an insertion or deletion, wherein one line may be referred to as having an insertion relative to a second line, or the second line may be referred to as having a deletion relative to the first line.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the chromosome 2 locus described herein may be introgressed into a recurrent parent that is susceptible to MRCV. The recurrent parent line with the introgressed gene or locus then has increased MRCV resistance.

As used herein, the term "linkage" is used to describe the degree with which one marker locus is associated with another marker locus or some other locus (for example, a MRCV locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units for cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits for bothloci. In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci cosegregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., increased MRCV resistance. The degree of linkage of a molecular marker to a phenotypic trait is measured, e.g. as a statistical probability of co-segregation of that molecular marker with the phenotype.

Linkage disequilibrium is most commonly assessed using the measure $r^2$, which is calculated using the formula described by Hill, W. G. and Robertson, A, Theor Appl. Genet 38:226-231 (1988). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie at al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

A "locus" is a position on a chromosome where a gene or marker is located.

"Maize" refers to a plant of the Zea mays L. ssp. mays and is also known as "corn".

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

"Mal de Rio Cuarto Virus (MRCV)" is a species of virus in the Reoviridae family, genus Fijivirus, which causes devastating crop losses for producers in Argentina.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, AFLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB Internet resource and the Arizona Genomics Institute Internet resource run by the University of Arizona.

Markers corresponding to genetic polymorphisms between members of a population can be detected by methods well-established in the art. These include, e.g., DNA sequencing, PCR-based sequence specific amplification methods, detection of RFLPs, detection of isozyme markers, detection of polynucleotide polymorphisms by allele specific hybridization (ASH), detection of amplified variable sequences of the plant genome, detection of selfsustained sequence replication, detection of SSRs, detection of SNPs, or detection of AFLPs. Well established methods are also known for the detection of expressed sequence tags (ESTs) and SSR markers derived from EST sequences and RAPDs.

A "marker allele", alternatively an "allele of a marker locus", can refer to one of a plurality of polymorphic nucleotide sequences found at a marker locus in a population that is polymorphic for the marker locus.

"Marker assisted selection" (MAS) is a process by which phenotypes are selected based on marker genotypes.

"Marker assisted counter-selection" is a process by which marker genotypes are used to identify plants that will not be selected, allowing them to be removed from a breeding program or planting.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic add sequence or molecule that can be used to identify the presence of a marker locus, e.g., a nucleic acid probe that is complementary to a marker locus sequence, through nucleic add hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e. genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a via a plant without the insertion. Thus, the marker need only indicate whether the indel region is present or absent. Any suitable marker detection technology may be used to identify such a hybridization marker, e.g., SNP technology is used in the examples provided herein.

The "Non-Stiff Stalk" heterotic group represents a major temperate heterotic group. It can also be referred to as the non-Iowa Stiff Stalk Synthetic for BSSS (non-BSSS) heterotic group.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate. "G" for guanylate or deoxyguanylate. "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

A "single nucleotide polymorphism (SNP)" is an allelic single nucleotide-A, T, C or G-variation within a DNA sequence representing one locus of at least two individuals of the same species,. For example, two sequenced DNA fragments representing the same locus from at least two individuals of the same species, AAGCCTA to AAGCTTA, contain a difference in a single nucleotide.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151-153 (1989)) with the default parameters (GAP PENALTY=10, GAP LENGTH PENALTY=10), Default parameters for pairwise alignments and calculation of percent identity of protein sequences using the Clustal V method are KTUPLE=1, GAP PENALTY=3, WINDOW=5 and DIAGONALS SAVED=5. For nucleic adds these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Genetic Mapping

It has been recognized for quite some time that specific genetic loci correlating with particular phenotypes, such as increased MRCV resistance, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as increased MRCV resistance. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each, marker locus for each line in the subpopulation. A significant marker-trait association indicates the dose proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Markers Associated with MRCV

Markers associated with increased MRCV resistance are identified herein. The methods involve detecting the presence of at least one marker allele associated with the enhanced resistance in the germplasm of a maize plant. The marker locus can be selected from any of the marker loci provided in Table 3, including PZA02272-3 and MAGI_105144, and any other marker linked to these markers (linked markers can be determined from the Maize GDB resource). The marker locus can be selected from any of the marker loci provided in Table 3, including PZA02272-3, DAS-PZ-11980, DAS-PZ-8644, DAS-PZ-10816, DAS-PZ-2849, zfl2-9, DAS-PZ-19494, Mo17-11696, and MAGI_105144 and any other marker linked to this marker (linked markers can be determined from the Maize GDB resource).

The genetic elements or genes located on a contiguous linear span of genomic DNA on a single chromosome are physically linked. PZA02272-3 and MAGI_105144, both highly associated with MRCV resistance, delineate an MRCV resistance QTL. Any polynucleotide that assembles to the contiguous DNA between and including SEQ ID NO:1 (the reference sequence for PZA02272-3), or a nucleotide sequence that is 95% identical to SEQ ID NO: 1 based on the Clustal V method of alignment, and SEQ ID NO:9 (the reference sequence for MAGI_105144), or a nucleotide sequence that is 95% identical to SEQ ID NO:9 based on the Clustal V method of alignment, can house marker loci that are associated with MRCV resistance.

The genetic elements or genes located on a contiguous linear span of genomic DNA on a single chromosome are physically linked for the subinterval of DAS-PZ-2849 and DAS-PZ-19494. DAS-PZ-2849 and DAS-PZ-19494, both highly associated with MRCV resistance, delineate a MRCV resistance QTL. Any polynucleotide that assembles to the contiguous DNA between and including SEQ ID NO:5 (the reference sequence for DAS-PZ-2849), or a nucleotide sequence that is 95% identical to SEQ ID NO:5 based on the Clustal V method of alignment, and SEQ ID NO:7 (the reference sequence for DAS-PZ-19494), or a nucleotide sequence that 95% identical to SEQ ID NO:7 based on the Clustal V method of alignment, can house marker loci that are associated with MRCV resistance.

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the markers listed in Table 3 can be used to predict MRCV resistance in a maize plant. This includes any marker within 50 cM of PZA02272-3, DAS-PZ-11980, DAS-PZ-8644, DAS-PZ-10816, DAS-PZ-2849, zfl2-9, DAS-PZ-19494, Mo17-11696, and MAGI_105144, the markers associated with MRCV resistance. The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8% 7%, 6%, 5%, 4%, 3%, 2% 1%, 0.75%, 0.5%, 0.25.degree., or less) are said to be "proximal to" each other.

Although particular marker alleles can show co-segregation with increased MRCV resistance, it is important to note that the marker locus is not necessarily responsible for the expression of the MRCV resistance phenotype. For example, it is not a requirement that the marker polynucleotide sequence be part of a gene that imparts increased MRCV resistance (for example, be part of the gene open reading frame). The association between a specific marker allele and the increased MRCV resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

The term "chromosomal interval" designates any and all intervals defined by any of the markers set forth in this invention. A chromosomal interval that correlates with MRCV resistance is provided. This interval, located on chromosome 2, comprises and is flanked by PZA02272-3 and MAGI_105144. A subinterval of chromosomal interval PZA02272-3 and MAGI_105144 is DAS-PZ-2849 and DAS-PZ-19494.

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for MRCV resistance. The interval described above encompasses a cluster of markers that co-segregate with MRCV resistance. The clustering of markers occurs in relatively small domains on the chromosomes, indicating the presence of a gene controlling the trait of interest in those chromosome regions.

The interval was drawn to encompass the markers that co-segregate with MRCV resistance. The interval encompasses markers that map within the interval as well as the markers that define the termini. For example, PZA02272-3 and MAGI_105144, separated by 7834272 bp based on the B73 reference genome, version 2, define a chromosomal interval encompassing a cluster of markers that co-segregate with MRCV resistance. A second example includes the subinterval, DAS-PZ-2849 and DAS-PZ-19494, separated by 1402949 bp based on the B73 reference genome, version 2, which defines a chromosomal interval encompassing a cluster of markers that co-segregate with MRCV resistance. An interval described by the terminal markers that define the endpoints of the interval will include the terminal markers and any marker localizing within that chromosomal domain, whether those markers are currently known or unknown.

Chromosomal intervals can also be defined by markers that are linked to (show linkage disequilibrium with) a marker of interest, and is a common measure of linkage disequilibrium (LD) in the context of association studies. If the $r^2$ value of LD between any chromosome 2 marker locus lying within the interval of PZA02272-3 and MAGI_105144, the subinterval of DAS-PZ-2849 and DAS-PZ-19494, or any other subinterval of PZA02272-3 and MAGI_105144, and an identified marker within that interval that has an allele associated with increased MRCV resistance is greater than ⅓ (Ardlie et al. Nature Reviews Genetics 3:299-309 (2002)), the loci are linked.

A marker of the invention can also be a combination of alleles at marker loci, otherwise known as a haplotype. The skilled artisan would expect that there might be additional polymorphic sites at marker loci in and around the chromosome 2 markers identified herein, wherein one, or more polymorphic sites is in linkage disequilibrium (LD) with an allele associated with increased MRCV resistance. Two particular alleles at different polymorphic sites are said to be in LD if the presence of the allele at one of the sites tends to predict the presence of the allele at the other site on the same chromosome (Stevens, Mol. Diag. 4:309-17 (1999)).

Marker Assisted Selection

Molecular markers can be used in a variety of, plant breeding applications (e.g. see Staub et al. (1996) Hortscience 729-741; Tanksley (1983) Plant Molecular Biology Reporter 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true with traits that are difficult to phenotype due to their dependence on environmental conditions. This category includes traits related to the resistance to biotic and abiotic stresses. This category also includes traits that are very expensive to phenotype because of laborious artificial inoculation or maintenance of managed stress environments. Another category of traits includes those which are associated with destruction of plant per se. Destructive phenotyping has been a bottleneck to implement MAS for the seed quality traits. Because DNA marker assays are not environmentally dependent, are robust, reliable, less laborious, less costly and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). Crop Sci; 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) Genetics 120:579-585). In classical breeding it is usually only by chance that recombinations are selected that contribute to a reduction in the size of the donor segment (Tanksley et al. (1989). Biotechnology 7: 257-264).

Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will avow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of the B73 reference genome, version 2 and the integrated linkage maps of the maize genome containing increasing densities of public maize markers, has facilitated maize genetic mapping and MAS. See, e.g. the IBM2 Neighbors maps, which are available online on the Maize GDB website.

The key components to the implementation of MAS are (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) Nucleic Acid Research 17: 6463-6471; Wang et al. (1994) Theoretical and Applied Genetics, 88:1-6). Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) Am J Hum Genet. 44:388-396), SSRs are highly suited to mapping and MAS as they are multi-allelic, codominant, reproducible and amenable to high throughput automation (Rafalski et al. (1996) Generating and using DNA markers in plants. In Non-mammalian genomic analysis: a practical guide. Academic Press, pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). Plant Mol Biol 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp, 475-492: Shi (2001) Clin Chem 47, pp. 164-172; Kwok (2000) Pharmacogenomics 1, pp. 95-100: Bhattramakki and Rafalski (2001) Discovery and application of single nucleotide polymorphism markers in plants. In: R, J Henry, Ed, Plant Genotyping: The DNA Fingerprinting of Plants, CABI Publishing, VVallingford. A wide range of commercially available technologies utilize these and other methods to interrogate SNPs including Masscode™. (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than, single SNPs and can be more descriptive of any particular genotype. For example, single SNP may be allele 'T' for a specific line or variety with increased GS tolerance, but the allele might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

The sequences listed in Table 3 can be readily used to obtain additional polymorphic SNPs (and other markers) within the QTL interval listed in this disclosure. Markers within the described map region can be hybridized to BACs or other genomic libraries, or electronically aligned with genome sequences, to find new sequences in the same approximate location as the described markers.

In addition to SSRs, FLPs and SNPs, as described above, other types of molecular markers are also widely used, including but not limited to, markers derived from EST sequences, RAPDs, and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species whose genomes share some level of colinearity at macro- and micro-level with maize, such as rice and sorghum.

In general, marker-assisted selection (MAS) uses polymorphic markers that have been identified as having a significant likelihood of co-segregation with MRCV resistance. Such markers are presumed to map near quantitative trait loci (QTL), give the plant its MRCV resistant phenotype, and are considered indicators, or markers, for the desired trait. Markers test maize plants for the presence of a desired allele, and those which contain a desired genotype at one or more loci are expected to transfer the desired genotype, along with a desired phenotype, to their progeny. Means for identifying a maize plant that has increased MRCV resistance are presented herein. As used herein, "means for identifying a maize plant that has increased MRCV resistace"include MRCV resistance-linked alleles at the marker loci PZA02272-3, DAS-PZ-11980, DAS-PZ-8644, DAS-PZ-10816 DAS-PZ-2849, zfl2-9, DAS-PZ-19494, Mo17-11696, and MAGI_ 105144. therefore, examples of "means for identifying a maize plant that has increased MRCV resistance"include the linked alleles set forth in Table 3: an adenine at nucleotide position 61 of SEQ ID NO:1 (PZA02272-3), a thymidine at nucleotide position 101 of SEQ ID NO:2 (DAS-PZ-11980),a cytosine at nucleotide position 101 of SEQ ID NO:3 (DAS-PZ-8644), a guanosine at nucleotide position 101 of SEQ ID NO:4 (DAS-PZ-10816), an adenine at nucleotide position 101 of SEQ ID NO:5 (DAS-PZ-2849), a cytosine at nucleotide position 61 of SEQ ID NO:6 (zfl2-9), an adenine at nucleotide position 101 of SEQ ID NO:7 (DAS-PZ-19494), a thymidine at nucleotide position 61 of SEQ ID NO:8 (Mo17-11696), and a guanosine at nucleotide position 61 of SEQ ID NO:9 (MAGI_ 105144).

The interval presented herein finds use in MAS to select plants that demonstrate increased MRCV resistance. Any marker that maps within the chromosome 2 interval defined by and including PZA02272-3 and MAGI_105144 can be used for this purpose. In addition, haplotypes comprising alleles at one or more marker loci within the chromosome 2 interval defined by and including PZA02272-3 and MAGI_105144 can be used to introduce increased MRCV resistance into maize lines or varieties. Any allele or haplotype that is in linkage disequilibrium with an allele associated with increased MRCV resistance can be used in MAS to select plants with increased MRCV resistance.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Plant Material

A Dow AgroSciences (DAS) elite line consistently displayed high levels of Mal de Rio Cuarto Virus (MRCV) resistance under infestation conditions. To identify QTL associated with this line that display a high correlation to MRCV resistance, a doubled haploid (DH) mapping population was developed and phenotypically evaluated in two endemic regions known to have high levels of viral outbreaks. QTL mapping analyses were completed using data collected over two successive years from the DH populations (Table1).

TABLE 1

Population size and SNP marker counts for the DH population evaluated for resistance to MRCV disease over two successive years.

| Mapping Populations | Year | Sample Size | SNP Marker Count |
|---|---|---|---|
| DH Population | 2010 | 163 | 509 |
| DH Population | 2011 | 173 | 446 |

Example 2

MRCV Disease Phenotype Evaluation

The DH mapping population was evaluated for MRCV symptomology in two endemic environments, Sampacho and Suco, Argentina. Two replicate sample populations were designed as randomized complete block studies (RCB). Plots were arranged in either two 3 meter (m) rows, or one 6 m row, with nearly 25 plants per DH line. In 2010, populations were planted on two separate dates to increase the chance of matching the stage of highest susceptibility of the corn plants with the highest peak of the vector population. In 2011, all populations were planted on three different planting dates spaced approximately one week apart for the same reason. Herbicide and fungicide treatments were used as needed for preventive control. In 2010, disease symptoms were evaluated at 20 days after flowering. In 2011, MRCV symptomology was assessed at three different time points over the course of the season in an effort to capture the timeframe that most accurately demonstrated a variable range of disease incidence. The intention was to capture phenotype data before disease pressure reached saturation. In both years, disease ratings were characterized using a percent incidence and a severity scale (MDG, Mean Disease Grade) as follows:

$$MDG = \Sigma_{i=0}^{5} fi \cdot xi$$

where fi: frequency of grade i, and xi: value of i-th grade. Grades are shown in Table 2.

TABLE 2

Descriptions of the Mean Disease Grade of MRCV.

| Grade | Symptoms |
|---|---|
| 0 | healthy plants; no symptoms |
| 1 | slight symptoms in upper leaves and tassels |
| 2 | moderate symptoms, slight height reduction, shortening of upper internodes and ear |
| 3 | stronger height reduction, multiple and conical ears, plant still productive but reduced yield |
| 4 | plant height severely reduced, multiple ears, scarce or null grain production due to ear reduction and malformations |
| 5 | dead plants; if still alive, extreme dwarfism, absence of ears, upper leaves and tassel |

Example 3

DNA Extraction and Single Nucleotide Polymorphic (SNP) Analysis

JoinMap® 3.0 (Van Ooijen et al., 2001) was used to develop a linkage map for subsequent QTL analysis. Interval mapping and composite interval mapping was conducted using MapQTL® 5.0 (Van Ooijen et al., 2002). A permutation test consisting of 1000 iterations was completed to determine the significant logarithm-of-odds (LOD) threshold value using a genome-widep value of 0.05. Loci with LOD scores greater than the calculated significant threshold were identified as potential QTL. The position with the largest LOD value on the linkage group was used as the estimated position of the QTL on the map.

A QTL was identified on chromosome 2 in the DH mapping population for both the Sampacho and Suco 2010 and 2011 data sets. The QTL was detected using the averaged 2011 phenotypic data from Sampacho and explained 27.9% of the variation for that environment. The QTL was detected using the averaged 2011 data from Suco and explained 45.9% of the variation in that environment. The chromosome 2 QTL is defined by the interval of PZA02272-3 and MAGI_105144, with the QTL peak defining the subinterval of DAS-PZ-2849 and DAS-PZ-19494 (Table 3).

Example 4

Marker Framework and Use for MAS

A set of common markers can be used to establish a framework for identifying markers in the QTL interval. Table 3 shows markers that are in consistent position relative to one another on the DAS internally derived map and the B73 reference genome, version 2. Physical locations of the DAS proprietary markers were determined using DAS proprietary GBrowser.

Closely linked markers flanking the locus of interest that have alleles in linkage disequilibrium with a favorable allele at that locus may be effectively used to select for progeny plants with increased MRCV resistance. Thus, the markers described herein, such as those listed in Table 3, as well as other markers genetically or physically mapped to the same chromosomal segment, may be used to select for maize plants with increased MRCV resistance. Typically, a set of these markers will be used (e.g. 2 or more, 3 or more, 4 or more, 5 or more) in the regions flanking the locus of interest. Optionally, a marker within the actual gene and/or locus may be used.

TABLE 3

Chromosome 2 interval and markers associated with MRCV resistance.

| Marker | SEQ ID NO. | SNP | Donor Allele | Physical Position (bp) |
|---|---|---|---|---|
| PZA02272-3 | 1 | A/G | A | 9962933 |
| DAS-PZ-11980 | 2 | T/A | T | 11217305 |
| DAS-PZ-8644 | 3 | C/G | C | 11418854 |
| DAS-PZ-10816 | 4 | G/A | G | 12103033 |
| DAS-PZ-2849 | 5 | A/G | A | 12255007 |
| zfl2-9 | 6 | A/C | C | 12644166 |
| DAS-PZ-19494 | 7 | A/T | A | 13657956 |
| Mo17-11696 | 8 | T/C | T | 15884180 |
| MAGI_105144 | 9 | A/G | G | 17797205 |

Physical positions were determined from the B73 reference genome, version 2.

REFERENCES

Di Renzo, M. A., Bonamico, N. C., Diaz, D. D., Ibañez, M. A., Faricell, M. E., Balzarini M. G. and Salerno, S. J. (2004). Microsatellite markers linked to QTL for resistance to Mal de Rio Cuarto disease in *Zea mays* L. J Agric Sci, 142:289-295.

Kreff, E.D., Pacheco, M. G., Diaz, D. G., Robredo, C. G., Puecher, D., Celiz, A., and Salerno, J. C. (2006). Resistance to Mal de Rio Cuarto Virus in maize: A QTL analysis. J Basic Appl Genet 17:41-50.

Martin, T., Franchino, J. A., Kreff, E. D., Procopiuk, A. M., Tomas, A., Luck, S. D., Shu, G. G. (2009). Major QTLs co

We claim:

1. A method for obtaining a maize plant that displays increased Mal de Rio Cuarto Virus (MRCV) resistance, the method comprising:

screening genomic DNA from a progeny maize plant for presence of a genetic marker linked to MRCV resistance located on maize chromosome 2 between nucleotide position 9,962,933 and nucleotide position 17,797,205, wherein the genetic marker linked to MRCV resistance is selected from the group consisting of:

an adenine (A) at nucleotide position 61 of SEQ ID NO:1, a thymidine (T) at nucleotide position 101 of SEQ ID NO:2, a cytosine (C) at nucleotide position 101 of SEQ ID NO:3, a guanosine (G) at nucleotide position 101 of SEQ ID NO:4,
an A at nucleotide position 101 of SEQ ID NO:5,
a C at nucleotide position 61 of SEQ ID NO:6,
an A at nucleotide position 101 of SEQ ID NO:7,
a T at nucleotide position 61 of SEQ ID NO:8, and
a G at nucleotide position 61 of SEQ ID NO:9; and
selecting the progeny maize plant if it comprises the genetic marker linked to MRCV resistance in its genomic DNA,
wherein the progeny maize plant is produced by crossing a first parental MRCV resistant maize plant with a second parental maize plant, wherein the first parental maize plant comprises the genetic marker linked to MRCV resistance, and wherein the second parental maize plant does not comprise the genetic marker linked to MRCV resistance.

2. The method according to claim 1, further comprising:
propagating the selected progeny maize plant comprising the genetic marker linked to MRCV resistance.

3. The method according to claim 1, the method further comprising:
backcrossing the selected progeny maize plant comprising the genetic marker linked to MRCV resistance with the second parental maize plant genotype for at least one cycle, to produce a backcross progeny maize plant comprising the genetic marker linked to MRCV resistance.

4. The method according to claim 3, wherein genomic DNA from the backcross progeny maize plant is screened for the genetic marker linked to MRCV resistance at each cycle.

5. A method for obtaining a maize plant that displays increased Mal de Rio Cuarto Virus (MRCV) resistance, the method comprising:
crossing a first parental MRCV resistant maize plant with a second parental maize plant, to produce progeny maize plants,
wherein the first parental maize plant comprises one or more genetic marker(s) linked to MRCV resistance located on maize chromosome 2 between nucleotide position 9,962,933 and nucleotide position 17,797,205, selected from the group consisting of:
an adenine (A) at nucleotide position 61 of SEQ ID NO:1,
a thymidine (T) at nucleotide position 101 of SEQ ID NO:2,
a cytosine (C) at nucleotide position 101 of SEQ ID NO:3,
a guanosine (G) at nucleotide position 101 of SEQ ID NO:4,
an A at nucleotide position 101 of SEQ ID NO:5,
a C at nucleotide position 61 of SEQ ID NO:6,
an A at nucleotide position 101 of SEQ ID NO:7,
a T at nucleotide position 61 of SEQ ID NO:8, and
a G at nucleotide position 61 of SEQ ID NO:9, and
wherein the second parental maize plant does not comprise the genetic marker(s) linked to MRCV resistance;
screening genomic DNA from a progeny maize plant for presence of the genetic marker(s) linked to MRCV resistance; and
selecting the progeny maize plant if it comprises the genetic marker(s) linked to MRCV resistance in its genomic DNA.

6. The method according to claim 1,
wherein the genomic DNA from the progeny maize plant is screened for presence of a plurality of genetic markers linked to MRCV resistance that are selected from the group consisting of an A at nucleotide position 61 of SEQ ID NO:1, a T at nucleotide position 101 of SEQ ID NO:2, a C at nucleotide position 101 of SEQ ID NO:3, a G at nucleotide position 101 of SEQ ID NO:4, an A at nucleotide position 101 of SEQ ID NO:5, a C at nucleotide position 61 of SEQ ID NO:6, an A at nucleotide position 101 of SEQ ID NO:7, a T at nucleotide position 61 of SEQ ID NO:8, and a G at nucleotide position 61 of SEQ ID NO:9, and
wherein the progeny maize plant is selected if it comprises the plurality of genetic markers linked to MRCV resistance in its genomic DNA.

7. The method according to claim 6, further comprising:
propagating the selected progeny maize plant comprising the plurality of genetic markers linked to MRCV resistance.

8. The method according to claim 6, the method further comprising:
backcrossing the selected progeny maize plant comprising the plurality of genetic markers linked to MRCV resistance with the second parental maize plant genotype for at least one cycle, to produce a backcross progeny maize plant comprising the plurality of genetic markers linked to MRCV resistance.

9. The method according to claim 8, wherein genomic DNA from the backcross progeny maize plant is screened for the plurality of genetic markers linked to MRCV resistance at each cycle.

* * * * *